(12) United States Patent
Wang et al.

(10) Patent No.: US 11,457,825 B2
(45) Date of Patent: Oct. 4, 2022

(54) CUFF-TYPE MONITORING DEVICE FOR MONITORING CARDIOVASCULAR PARAMETERS

(71) Applicant: WITHINGS, Issy les Moulineaux (FR)

(72) Inventors: Jean-Louis Wang, Puteaux (FR); Xianzhi Zhang, Paris (FR); Virginie Vissac, Plaisir (FR); Pierre-Antoine Cuniasse, Bagneux (FR); Benoit Tucoulat, Paris (FR); Mélanie Alsberghe-Patel, Paris (FR)

(73) Assignee: WITHINGS, Issy les Moulineaux (FR)

( * ) Notice: Subject to any disclaimer, the term of this patent is extended or adjusted under 35 U.S.C. 154(b) by 350 days.

(21) Appl. No.: 16/719,592

(22) Filed: Dec. 18, 2019

(65) Prior Publication Data
US 2020/0214577 A1 Jul. 9, 2020

(30) Foreign Application Priority Data
Jan. 4, 2019 (EP) .................................... 19305009

(51) Int. Cl.
*A61B 5/021* (2006.01)
*A61B 5/318* (2021.01)

(52) U.S. Cl.
CPC .......... *A61B 5/02141* (2013.01); *A61B 5/318* (2021.01); *A61B 2562/0204* (2013.01); *A61B 2562/0247* (2013.01)

(58) Field of Classification Search
CPC .... A61B 2560/0425; A61B 2560/0443; A61B 2562/0204; A61B 2562/0247;
(Continued)

(56) References Cited

U.S. PATENT DOCUMENTS

| | | |
|---|---|---|
| 3,906,937 A | 9/1975 | Aronson |
| 5,865,761 A | 2/1999 | Inukai et al. |

(Continued)

FOREIGN PATENT DOCUMENTS

| | | | |
|---|---|---|---|
| EP | 3375358 A1 | | 9/2018 |
| WO | WO2018167362 | * | 9/2018 |

OTHER PUBLICATIONS

European Search Report Application No. EP 19305009.3 dated Jun. 21, 2019.

*Primary Examiner* — Jonathan T Kuo
(74) *Attorney, Agent, or Firm* — Pillsbury Winthrop Shaw Pittman LLP

(57) ABSTRACT

A cuff-type monitoring device, for collecting cardiovascular data relating to an individual user, comprising a control unit housing and a cuff assembly coupled or attached to the control unit housing, the cuff assembly comprising an inner layer, an inflatable bladder, a cuff holder, forming an structural resilient armature of the cuff assembly, an intermediate sheet, an outer band, wherein the cuff assembly is configured, in use, to surround a upper limb of the individual, with the inner layer in contact with the upper limb, wherein control unit housing comprises at least a pump configured to inflate the inflatable bladder, wherein the intermediate sheet is made in an inextensible, i.e. non-stretchable, fabric and there is provided a border joint or seam at least on three sides on a peripheral border of the inflatable bladder, the border joint joining and securing together the inner layer, the inflatable bladder, the intermediate sheet, and the an outer band.

19 Claims, 8 Drawing Sheets

(58) Field of Classification Search
CPC . A61B 5/02125; A61B 5/02141; A61B 5/022; A61B 5/02233; A61B 5/282; A61B 5/318; A61B 5/681; A61B 5/6831; A61B 7/003; A61B 7/04
See application file for complete search history.

(56) References Cited

U.S. PATENT DOCUMENTS

| | | | |
|---|---|---|---|
| 7,955,352 B2 * | 6/2011 | McEwen | A61B 17/1322 606/202 |
| 2007/0032818 A1 * | 2/2007 | McEwen | A61B 17/1322 606/202 |
| 2011/0282222 A1 | 11/2011 | Cehn et al. | |

* cited by examiner

CUFF-TYPE MONITORING DEVICE FOR MONITORING CARDIOVASCULAR PARAMETERS

CROSS-REFERENCE TO RELATED APPLICATION

This application claims priority under the Paris Convention to European Patent Application No. 19305009.3 filed on Jan. 4, 2019.

FIELD OF THE DISCLOSURE

The present disclosure relates to devices for analysing cardiovascular parameters of an individual. More particularly, it relates to a multifunction cuff device for monitoring cardiovascular parameters of such individual.

BACKGROUND OF THE DISCLOSURE

Such device is configured to collect cardiovascular parameters like blood pressure and at least one additional signal, in particular an electrical signal representative of an electrocardiogram or an acoustic signal representative of a phonocardiogram. More specifically, there is provided a cuff comprising at least an inflatable bladder to pressurize the arm of the patient. The pressure prevailing in the bladder is monitored in real time to collect blood flow data. More precisely a pressure sensor is provided which measures the pressure and pressure variations thereof, the latter being reflective of the blood flow and heart's activity.

This monitoring process occurs either during inflation phase or in deflation phase, or both. It has been found that a slip-stick phenomenon is detrimental to the accuracy of the measurement. Deformation of the cuff device under inflation (or deflation) changes the mechanical constraints applied to the layers constitutive of the cuff. As a result, the layers tend to move with respect to one another. Due to the friction forces between the compressed layers, this movement is jerky. This phenomenon is known as slip-stick. It impedes the measurement of blood pressure. In addition, small sudden geometry change(s) of the bladder, like the unfolding of a small pocket of the bladder, result in pressure variation(s) that interferes with variations induced by blood flow, therefore undermining the quality of the collected signal and data. The detrimental phenomenon mentioned above is illustrated at FIG. 14 where a small sudden geometry change(s) of the bladder impact the pressure curve and the variations thereof.

The inventors have endeavored to bring improvement(s) to these matters.

SUMMARY OF THE DISCLOSURE

According to a first aspect of the present disclosure, it is disclosed a cuff-type monitoring device, for collecting cardiovascular data relating to an individual user, comprising a control unit housing (7) and a cuff assembly (18) coupled to the control unit housing, the cuff assembly comprising, from an inner item to an outermost item:
an inflatable bladder (2),
a cuff holder (3), forming a structural resilient armature of the cuff assembly,
an intermediate sheet (4),
an outer band (5),
wherein the cuff assembly is configured, in use, to surround an upper limb of the individual, with the inner layer in contact with the upper limb,
wherein the control unit housing comprises at least a pump configured to inflate the inflatable bladder,
wherein the intermediate sheet is made in a non-stretchable (inextensible) fabric and there is provided a border joint at least on three sides on a peripheral border of the inflatable bladder, the border joint joining and securing together the inflatable bladder (2), the intermediate sheet (4), and the outer band (5).

Thanks to these dispositions, a four-layer assembly is provided which allows smooth inflation and deflation. Inflation and deflation are carried out without slip-stick phenomenon. Particularly, the non-stretchable intermediate sheet has been found beneficial to prevent sudden small slide movement. The border joint advantageously limits the movement(s) of the cuff holder in the cuff assembly.

In the present document, the geometric reference may be defined as follows: longitudinal axis of the cuff assembly when flat is denoted L, transverse axis is denoted W and corresponds to the height of the device along the limb in use, thickness direction is denoted Y which is perpendicular to the layers comprised in the assembly.

The intermediate sheet may be made in a nylon fabric.

Besides, one or more of the following features can be used optionally, alone or in combination.

According to a particular option, the cuff assembly further comprises, as innermost item, an inner layer (1), configured to come in contact, directly or via a clothing, with the upper limb. In this configuration, the border joint joins and secures the inner layer (1) together with the inflatable bladder (2), the intermediate sheet (4), and the outer band (5).

The inner layer may be made in lycra.

According to a particular option, there is provided a first opening in the intermediate sheet and in the outer band to let the passage for at least one fluid port (99) of the inflatable bladder.

According to a particular option, the cuff assembly is fixed to the control unit housing, and there are provided second openings in the intermediate sheet and in the outer band to let the passage for at least two hooks of the cuff holder, said hooks being configured to be retained in the control unit housing or an attachment member thereof.

According to a particular option, the border joint is a border seam.

There may be provided a further seam on the fourth side, made after inserting the cuff holder. This fourth seam advantageously further limits the movement(s) of the cuff holder in the cuff assembly.

According to a particular option, the border joint is made by ultrasonic or thermal welding. This is a possible alternative to a seam technique, if the materials are compatible with such ultrasonic or thermal welding.

According to a particular option, the intermediate sheet exhibits a Young modulus not less than 1 giga Pascal.

According to a particular option, the device may further comprise an acoustic sensor (90) coupled to the external wall of the cuff assembly and having a sensitive side (91) oriented away from the internal wall of the cuff assembly.

According to a particular option, the device may further comprise a set of contact electrodes (3) for electrocardiographic sensing, the set of contact electrodes (3) comprising at least first and second contact electrodes (31,32) for electrocardiographic sensing, the first electrode (31) being arranged in the internal wall of the cuff assembly, the second electrode being arranged in a position easily accessible by a hand of the user. In one option the second electrode is on the external wall of the control unit housing (7). In another option it is on the outer band (5).

Therefore the first contact electrode benefits from the pressure exerted by the cuff which optimizes the quality of the contact and thus the quality of the ECG measurement. Electric signals from these ECG electrodes can be used to detect the P wave, QRS complex, and T wave, and to detect anomalies with the rhythm of the heart activity. When the device is installed at the left upper limb or left arm of the user, the second electrode is easily accessible by the right hand (MD) of the user.

According to a particular option, the set of contact electrodes (3) comprises a third contact electrode (33), arranged in the internal wall of the cuff assembly. This third contact electrode serves as a further contact point allowing to inject an inverse voltage reference in to the body, said inverse voltage being an inverse of an average voltage acquired at the two first electrodes. This improves quality and electrical immunity of the resulting ECG.

The control unit housing may be attached to the cuff assembly via an interface member, which provides mechanical secure attachment, electrical coupling and pneumatic coupling.

According to a particular option, the cuff holder can be a resilient plastic sheet, with a first longitudinal end (35) coupled to the control unit housing (or to the interface member thereof) and a second end (36) having a tapered end portion (decreasing thickness) down to the edge. Thereby, more flexibility is provided at the distal end and this allows easy bending at this place. This favors a circular shape around the arm. The tapered end portion also reduces the risks of slip-stick. This is particularly advantageous in the presence of the electrodes 31, 33 at this end of the cuff.

According to a particular option, the cuff holder (3) can be a monolithic resilient part.

According to a particular option, the first and third electrodes 31,33 are arranged at a cuff assembly distal end (second end 36) opposed to the interface member.

According to a particular option, the second electrode (32) covers at least the bottom part of the control unit assembly cylinder over at least 130° about Z, over at least 20% of the height H7. Likewise, the second electrode can be naturally seized by the right hand of the user, hence giving way to a good contact quality at this place.

Regarding dimensions, at flat configuration, the length L1 of the cuff assembly along the longitudinal direction L can be comprised between 20 cm and 40 cm. The height H1 along the transverse axis W direction can be comprised between 10 cm and 20 cm.

According to a particular option, the device may further comprise an attachment band (8), extending from the cuff assembly along the longitudinal direction (L), the attachment band being flexible and having fixing means configured to momentarily secure the attachment band to the outer band of the cuff assembly during a measurement cycle. This allows convenient attachment whatever the size of the arm/limb.

The attachment band may include at least a prolongation of the inner layer and a prolongation of the outer layer, but not including inflatable bladder.

The attachment band can be an extension/prolongation of the cuff assembly but without resilience. The cuff assembly has a structural resilience, whereas the attachment band exhibits few or no structural resilience, in particular in the general bending direction.

There are provided fixing means which may comprise loop and hook pads, a loop pad (88) at one location and a hook pad (89) at another, counterpart location, such that adjustment and securing of various encompassed circumferences ($\pi$ D2) of user's arm is made available. Loop pad can be arranged at the attachment band (8). Hook pad can be arranged at the outer wall of the cuff assembly. Loop and hook pads can be formed by Velcro™ or the like.

There are provided a magnet (58) on one part and metallic or ferrite members (59) on a counterpart to maintain attachment band (8) against the cuff assembly at a stowed configuration.

According to a particular option, the device may further comprise connection wires (44,45,49) to electrically couple the contact electrodes and/or the acoustic sensor with the control unit housing. Advantageously, the wires are integrated into the cuff assembly and they are protected therein and not visible from the outside.

According to a particular option, the connection wires are arranged at an outer zone of the bladder, for example between the intermediate sheet (4), and the outer band (5). Such position for connection wires prevents measurement hindrance. Such position avoids possible mechanical damage to connection wires.

According to a particular option, the control unit housing (7), the attachment band (8) and the cuff assembly have substantially the same height (H3,H1,H7) along the transverse axis W. This provides an aesthetic assembly and eases rollup configuration. This configuration allows optimization of the occupied volume.

According to a particular option, the control unit housing comprises a pneumatic unit which comprises a discharge valve, a check valve, and a pressure sensor. Thereby, the relevant pneumatic equipment is integrated into the control unit housing, this enabling to make accurate pressure measurements.

According to a particular option, the control unit housing can comprise an electronic controller configured to control the pneumatic unit and to determine at least the arterial pressure of the user, an On/Off switch (71) and a display (77), The user can start himself/herself the measurement cycle, and the results are provided directly for the user.

According to one particular option, the control unit housing is generally cylindrical, having a diameter D7<40 mm. Advantageously, this turns to be a compact solution which accommodates all the necessary components for the measurement, including a battery for autonomous use.

According to a particular option, the control unit housing and the acoustic sensor are arranged at an angle $\alpha$ comprised between 90° and 140° with regard to the cylindrical configuration of the cuff assembly, as defined in a use configuration on a 30 cm reference arm circumference. It proves to be a particularly convenient and user-friendly spatial arrangement. This is a natural position for having the acoustic waves sensed against the chest and received by the electronic controller through the acoustic sensor.

According to a particular option, the bladder walls have low friction coefficient, their outer surface can be texturized.

According to a particular option, the first and third ECG electrodes are arranged at the distal end, one after the other along the transverse direction W.

The present disclosure is also directed to a system for monitoring cardiovascular parameters of an individual user, comprising a cuff-type device as defined above, and a smartphone configured to run an application configured to enable the user to enter contextual data and to display at least cardiovascular parameters history for the individual user.

BRIEF DESCRIPTION OF THE DRAWINGS

Other features and advantages of the disclosure appear from the following detailed description of one of its embodiments, given by way of non-limiting example, and with reference to the accompanying drawings, in which.

DETAILED DESCRIPTION OF THE DISCLOSURE

In the figures, the same references denote identical or similar elements. For clarity purposes, some parts are represented intentionally not at scale with regard to other parts. Also, some parts of timing charts can be represented intentionally not at scale.

Figure 1:
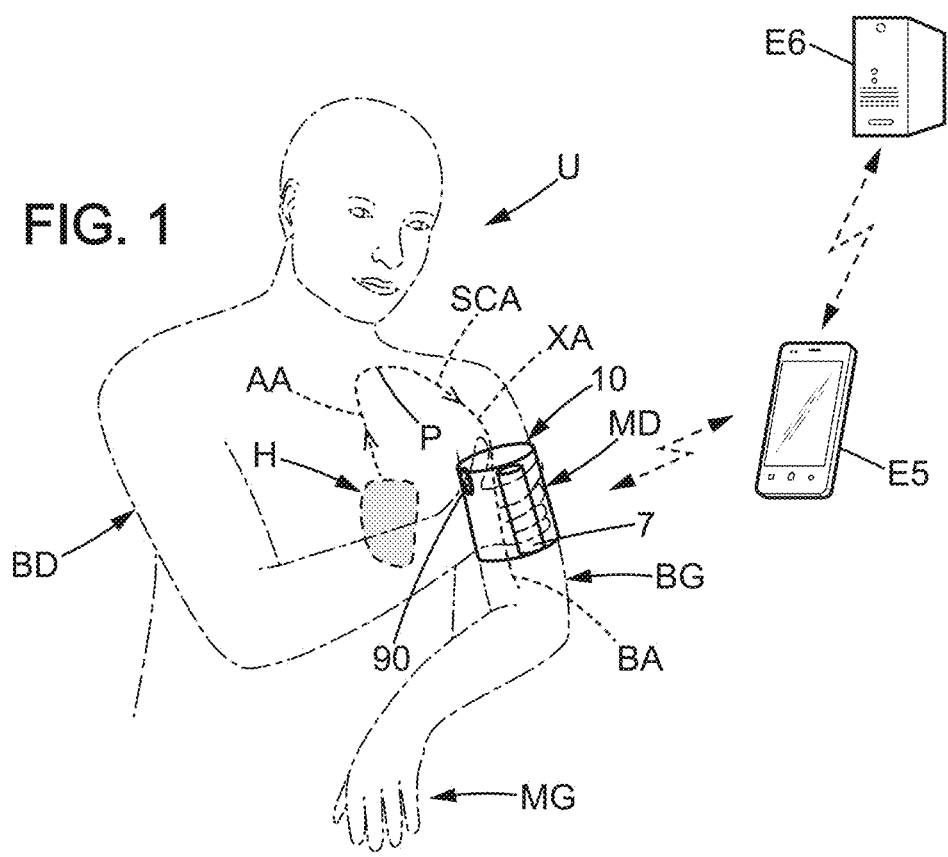
FIG. 1 illustrates a general overview of a device according to the present disclosure in a use configuration.

FIG. 1 shows an individual (also 'user') U in a configuration where he/she is using a monitoring device according to the present disclosure. The device (otherwise called "apparatus") looks like a known brachial blood pressure sensing device (commonly named Blood Pressure Monitor i.e. in short "BP Monitor"), but the device exhibits extended functionalities as will be apparent below, so that the device can be called 'upgraded BP Monitor'.

The user U in question has, among other organs and limbs in his/her anatomy: a left arm BG, a right arm BD, a heart H, a left hand MG a right hand MD.

Further the user in question has an aortic artery ('aortic arch') denoted AA, a subclavian artery SCA, an axillary artery XA, a brachial artery BA, belonging generally to the cardiovascular system of the user. Therefore a blood path of interest noted P is defined as the fluid conduit from the heart H to a reference point at the brachial artery BA.

The device 10 has a wireless communication capability to exchange data with a mobile entity like a smartphone E5 (more generally a mobile device belonging to the user U like a tablet, a laptop . . . ) Such smartphone E5 may in turn exchange data with a remote entity like an Internet server E6 (more generally any resource available somewhere in Internet, not excluding a so-called "cloud" resource).

The monitoring device 10 has either a small display or no display at all, since the user interface capability provided by the smartphone E5 is fully relevant to support displays relating to the use and extended functionalities of the device.

The monitoring device 10 is intended to be used at a home environment, for healthy people as well as people suffering from some disease. It may be used in a medical environment but is particularly suitable to be used by non-medical personnel, i.e. the user under measurement him/herself.

The monitoring device 10 comprises a cuff assembly 18 wrapped around the arm BG and a control unit housing 7, The cuff assembly 18 will be described in more details later. The cuff assembly 18 is coupled to the control unit housing 7 via an interface member 6 whose purpose and details will be given later.

The rest of the time, when not in use, the monitoring device can be stowed, notably in a folded configuration as will be seen later.

As illustrated on FIG. 1, the device comprises a cuff assembly ('armband' can also be used) wrapped around the arm i.e. the part of the upper limb comprised between the shoulder and the elbow.

In another configuration or variant, the device can be used elsewhere, at the forearm for example, or at the wrist. Generally speaking, the cuff assembly 18 is configured, in use, to surround an upper limb of the user.

As illustrated on FIG. 1, the device is installed on the left arm of the user. However it is not excluded to use the device elsewhere, at the right upper limb for example.

Figure 2:
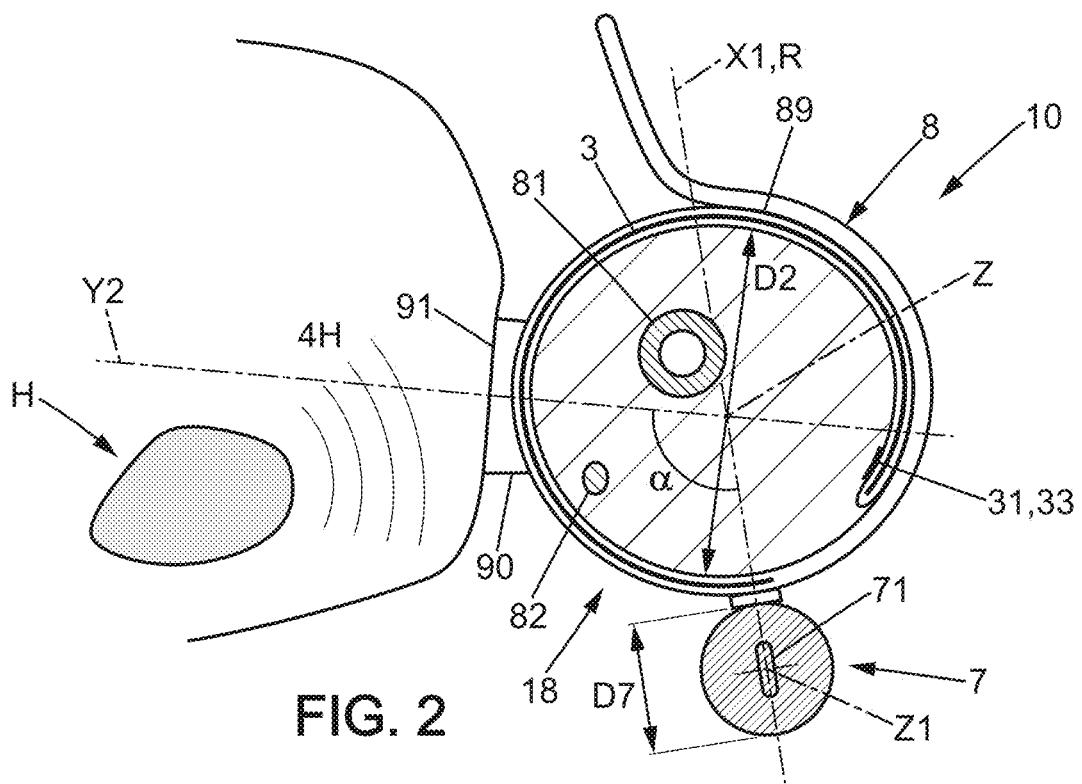
FIG. 2 shows a diagrammatic sectional view of the device in place on the left arm of the user, and adjacent to the chest, for the generically defined embodiment.

As illustrated on FIG. 2, the left arm of the user includes a bone named humerus denoted 81, muscles (not especially shown), and the above mentioned brachial artery denoted 82. The humerus extends along an axis denoted Z. The cuff assembly 18, when wrapped around the arm BG, has a general cylindrical shape with a reference axis substantially coinciding with arm axis Z.

Cuff Assembly

Figure 3:
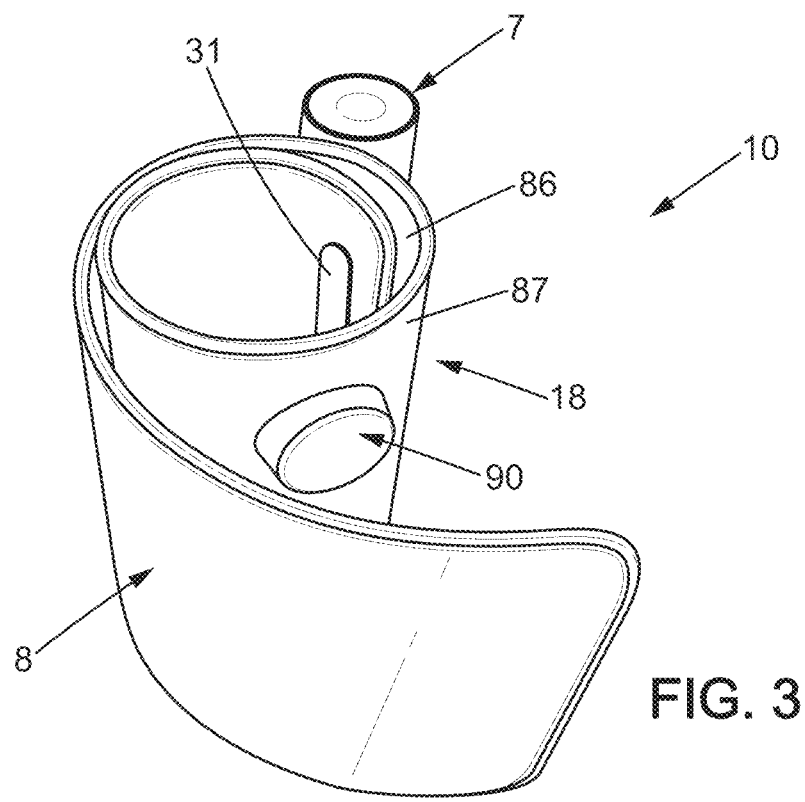
FIG. 3 illustrates a picture of the device when not in use.
Figure 4:
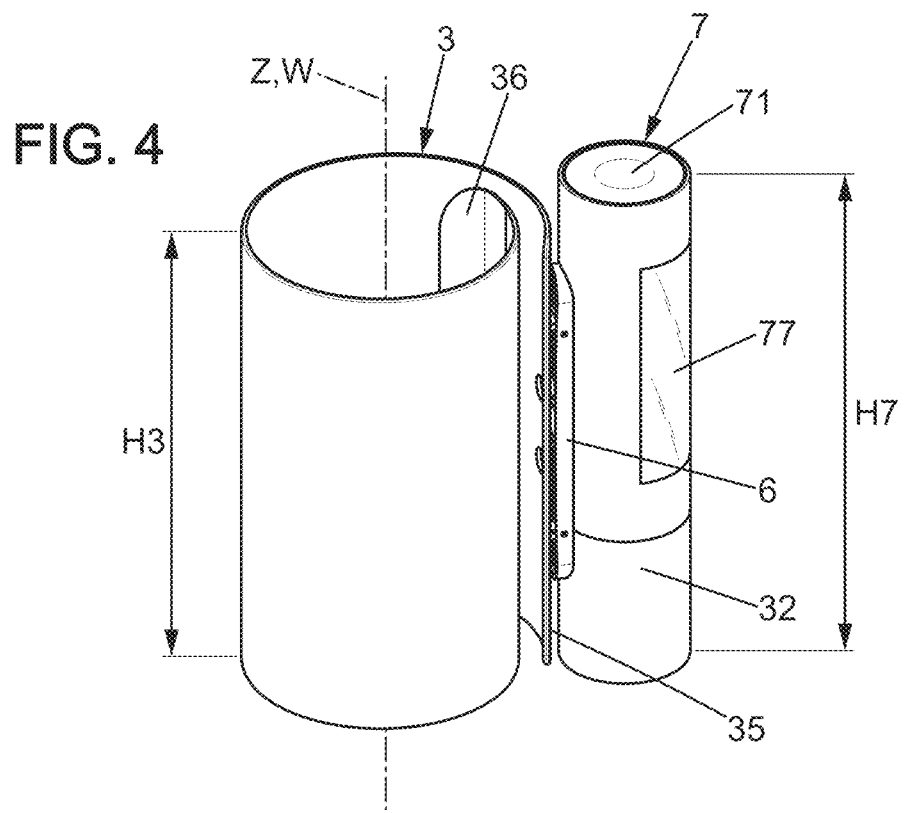
FIG. 4 shows partially the monitoring device illustrating in particular a control unit housing and a resilient cuff holder attached via an interface member.
Figure 5:
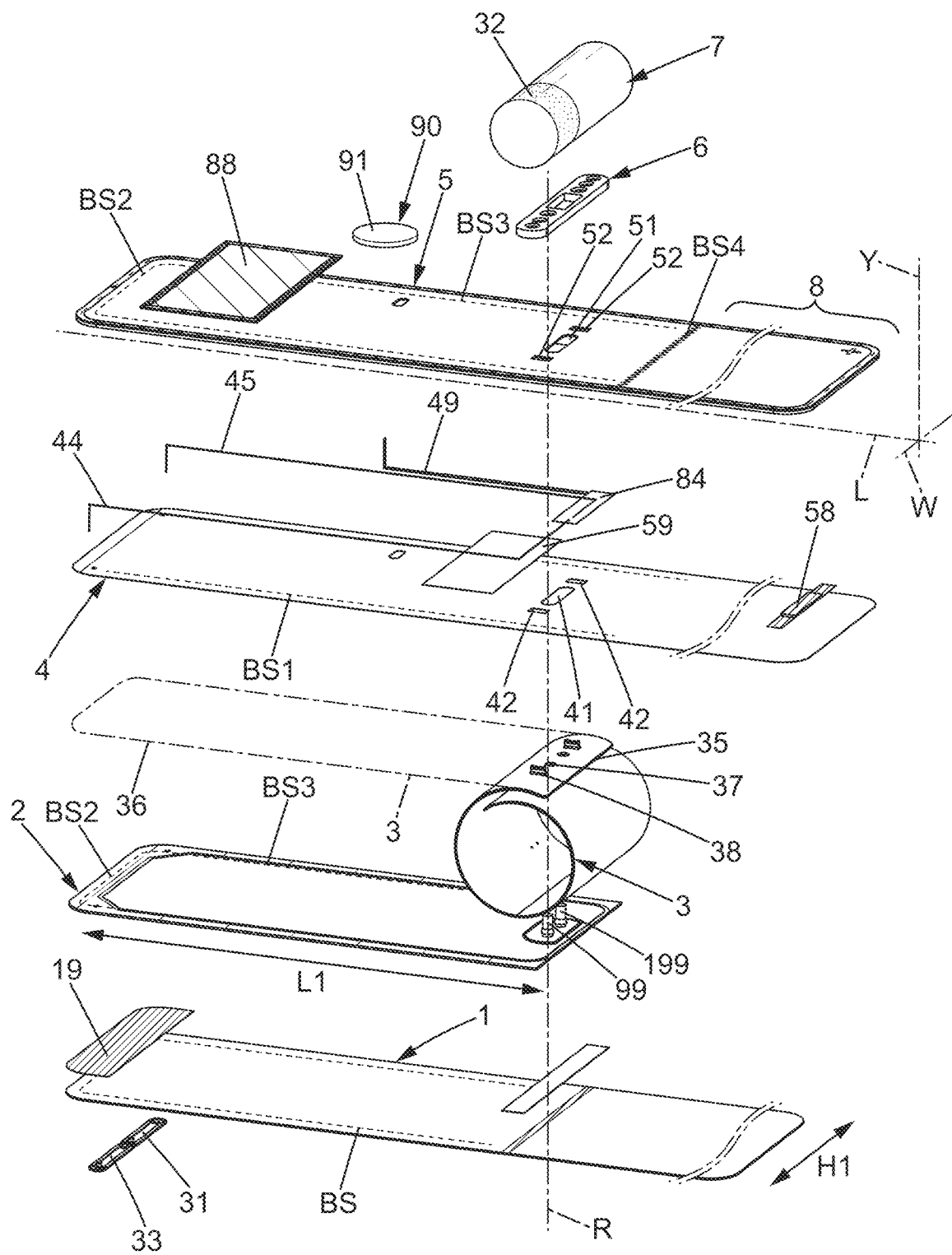
FIG. 5 shows an exploded view of the monitoring device.

As shown at FIGS. 3 to 5, the cuff assembly 18 comprises, from an innermost item to an outermost item, at least the following components:
an inner layer, denoted 1,
an inflatable bladder, denoted 2,
a cuff holder, denoted 3,
an intermediate sheet, denoted 4,
an outer band, denoted 5.

Regarding overall dimensions of the cuff assembly 18, at flat developed configuration, the length L1 of the cuff assembly along the longitudinal direction L can be comprised between 20 cm and 40 cm. The height H1 along the transverse axis W direction can be comprised between 10 cm and 20 cm.

The inner layer 1 is a thin fabric layer. The inner layer 1 may be made in lycra. Lycra turns out to be a comfortable material, not prone to collect dirt and/or sweat. The inner layer 1 is optional in the frame of the present invention, in particular when the outer wall of the bladder 2 directed inwardly 2 is texturized (likewise 'textured').

Figure 13:
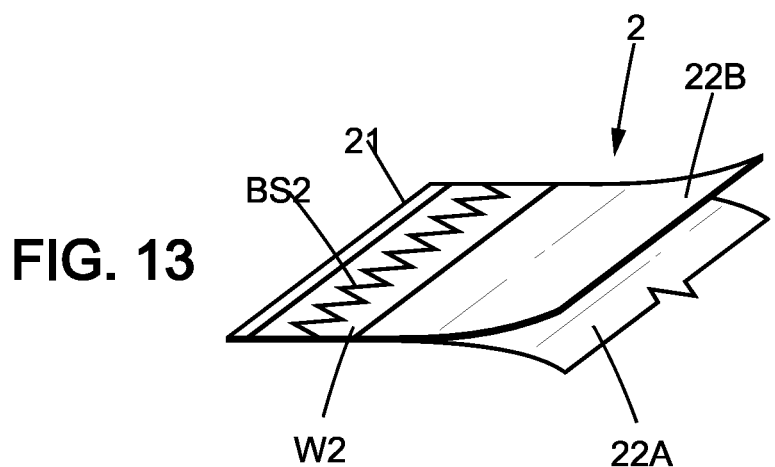
FIG. 13 is a partial detailed view of a border seams at the bladder welded edge.
Figure 14:
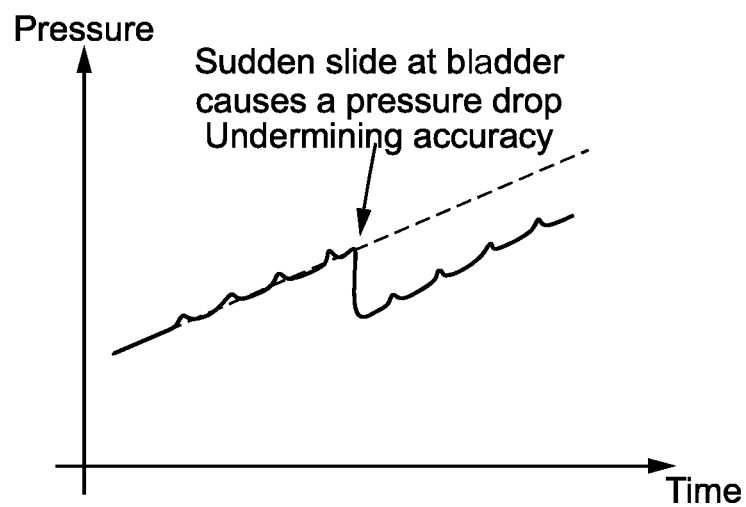
FIG. 14 illustrates the prior art where a small sudden geometry change of the bladder undermines the quality of the collected signal and data.

The inflatable bladder 2 is made from two sheets 2A,2B of plastic material (for instance PVC, TPU, PA, etc.) arranged one atop another in a main plane and are welded together at their peripheral border. FIG. 13 illustrates an edge 21 of the inflatable bladder where the two sheets 2A,2B are welded together thanks to border weld W2. Further there is shown a border seam BS that will be discussed later.

The inflatable bladder 2 has two fluid connection ports denoted 99,199. One port is for inflating, deflating, whereas the other one is dedicated to a measuring channel, so that the pressure measured is not perturbed by the unsteady flow of the pump during inflation.

In other configurations, there may be only one port for both functions.

The connection ports denoted 99,199 extend perpendicularly to the main plane, along the thickness direction Y of the cuff assembly and along the assembling direction R of interface member 6. Air volume at nominal inflated state can be comprise between 0.05 liter and 0.2 liter.

The cuff holder 3 forms a structural resilient armature of the cuff assembly. The cuff holder is a resilient plastic sheet, with a first longitudinal end 35 attached to the control unit housing/interface member and a second end 36 having a tapered end portion, i.e. with a decreasing thickness to the edge; the first longitudinal end 35 is called proximal and the second end 36 is called distal.

The dimensions of the cuff holder at flat configuration are slightly less than the corresponding dimensions of the bladder.

The thickness of the cuff holder can be comprised between 0.5 mm and 3 mm.

The cuff holder can be made out of polypropylene.

The second end 36 has advantageously a tapered end portion, i.e. a decreasing thickness down to the edge.

The resilient cuff holder 3 comprises two retaining members 38 at the first longitudinal end 35. In the shown example, the retaining members are formed as hooks, arranged in symmetry with regard to a median plane Tm.

The hook is arranged at an end of a hook arm. In the shown example, there is provided a large footprint for these hook arms, with a rounded shape 34, also named 'fillet'. The foot/shoe is therefore larger than the hook arm profile itself. It provides a strong implant on the cuff holder sheet.

The resilient cuff holder 3 comprises two through-holes 37, configured to let a suitable passage for the fluid ports 99,199 of the inflatable bladder.

The resilient cuff holder 3 comprises protrusions 39 providing a socket for the attachment of the acoustic sensor 90 and its mechanical securing thereto.

The intermediate sheet 4 is made in an inextensible, i.e. non-stretch fabric.

The intermediate sheet 4 may be made in a nylon fabric.

Regarding the inextensibility ("non stretchable" feature) of the fabric composing the intermediate sheet 4, the Young modulus of the nylon fabric here is typically between 1 and 3 Gpa (giga Pascals).

Besides, for the purpose of letting a passage for the one or two fluid ports 99,199 of the inflatable bladder, there is provided a first opening 41 in the intermediate sheet 4 as illustrated at FIG. 5.

Further, when the cuff assembly 18 is fixed to the control unit housing, and there are provided second openings 42 in the intermediate sheet 4 to let the passage for at least two hooks of the cuff holder, said hooks being configured to be retained in the control unit housing 7 or an attachment member 6 thereof.

The outer band 5 constitutes the external layer of the cuff assembly. The outer band 5 can comprise one or more foamed areas.

In one shown embodiment, the outer band 5 comprises a TPU foam layer having a thickness between 0.1 and 0.6 mm and a nylon fabric arranged at the outer face.

The outer band. 5 can comprise fixing means (hooks or loops or the like). In one shown embodiment the outer band 5 comprises a hook pad 89 at the outer surface thereof.

There may be provided a magnet 58 or ferrite 59 under the outer band 5 for rollover stowed configuration. However, the magnet and ferrite or metal can be accommodated in other layer(s) for example at the intermediate sheet 4.

The outer band 5 can comprise an extension beyond the cuff assembly forming part or all of an attachment band 8 discussed later.

Besides, for the purpose of letting a passage for the one or two fluid ports 99,199 of the inflatable bladder, there is provided a first opening 51 in the outer band 5 as illustrated at FIG. 5.

Further, when the cuff assembly 18 is fixed to the control unit housing, and there are provided second openings 52 in the outer band 5 to let the passage for at least two hooks of the cuff holder, said hooks being configured to be retained in the control unit housing 7 or an attachment member 6 thereof.

Border Joint or Seam

There is provided a border joint at least on three sides on a peripheral border of the inflatable bladder, the border joint joining and securing together the inner layer 1 (optionally though), the inflatable bladder 2, the intermediate sheet 4, and the an outer band 5.

In the shown example, the border joint is a border seam. There are provided a first border seam BS1, a second border seam BS2, and a third border seam BS3, and optionally a fourth border seam BS4, said seams being collectively denoted BS.

It is contemplated that one of the border seams, either BS2 or BS4, can be made after the cuff holder 3 has been inserted inside the cuff assembly between the bladder 2 and the intermediate sheet 4.

According to an alternative solution, instead of making a seam, it is possible to use a technique of ultrasonic or thermal welding.

Further, when the cuff assembly 18 is fixed to the control unit housing, and there are provided second openings 42 in the intermediate sheet 4 and further second openings 52 in the outer band 5 to let the passage for at least two hooks of the cuff holder, said hooks being configured to be retained in the control unit housing 7 or an attachment member 6 thereof.

Figure 12:
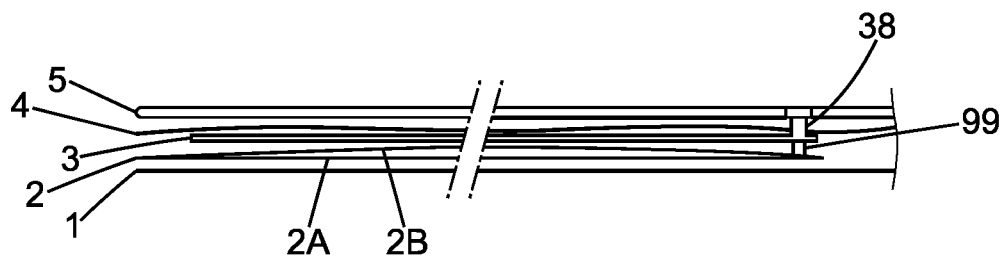
FIG. 12 shows a cross-sectional partial schematic view of the cuff assembly, illustrating the various items as separate layers before assembly.

As illustrated at FIG. 12, the following items, formed as separate and distinct parts, from an innermost item to an outermost item, (namely the inner layer 1, the inflatable bladder 2, the intermediate sheet 4 and the outer band 5) are disposed one atop another in a main plane, and exhibit substantially the same length at flat configuration. A weld or seam is then carried out at the peripheral border of the above parts.

We note however that the length of the cuff holder 3 is slightly less since it is not taken in the seam process.

Control Unit Housing

Figure 11:
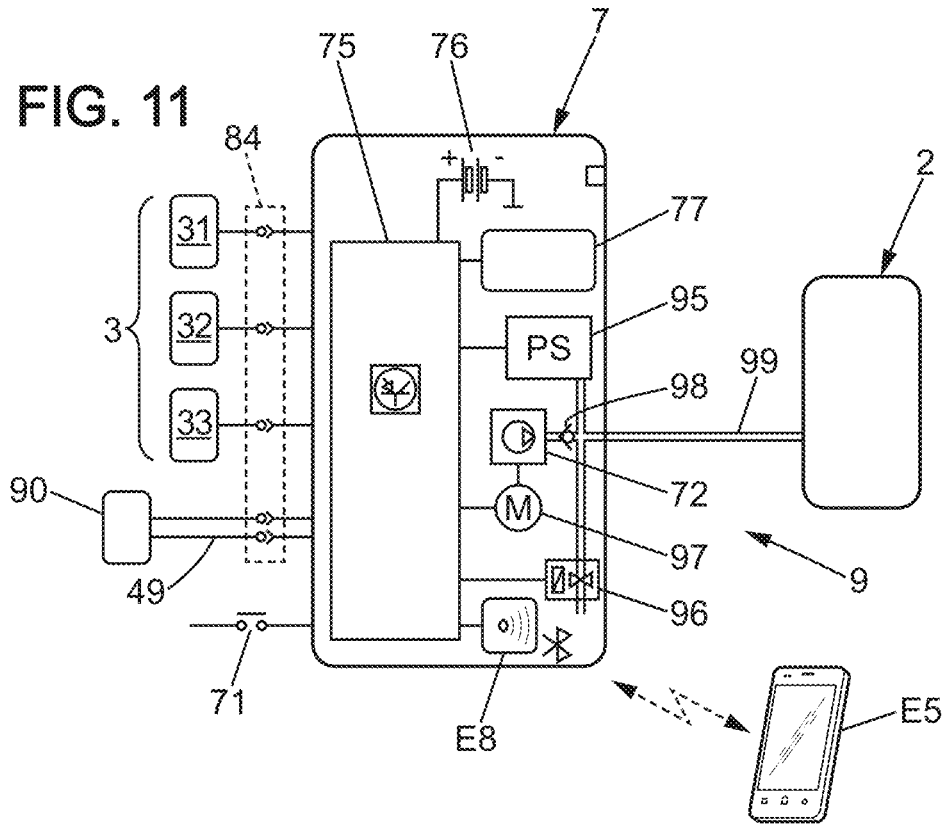
FIG. 11 shows a functional block diagram.

As apparent from FIG. 11, the control unit housing 7 comprises a pneumatic unit 9.

The control unit housing 7 comprises an electronic controller 75 configured to control the pneumatic unit and to determine at least the arterial pressure of the user, The control unit housing 7 comprises an On/Off switch 71 and a display 77.

The pneumatic unit 9 comprises the already mentioned pump 72 driven by an electrical motor 97, a discharge valve 96, a check valve 98, and a pressure sensor 95.

The control unit housing 7 exhibits generally a cylindrical shape. The diameter D7 of the control unit housing 7 is less than 40 min, which turns out to be a compact solution which accommodates all the necessary components for the measurement, including a battery 76 for autonomous use.

Sensors (Stetho and ECG)

The device 10 may comprise additionally an acoustic sensor denoted 90.

The cuff assembly 18 has an internal wall denoted 86 intended to contact the arm's skin (or light clothing) and to press against the arm. The armband has an external wall denoted 87 on the opposite side of the band with regard to the internal wall 86.

In use configuration, the acoustic sensor 90 is located against the chest, i.e. the left side of chest. Sound waves 4H emitted by the heart are sensed by a sensitive portion 91 of the acoustic sensor 90 the sensitive portion 91 bearing on the left-side chest, i.e. adjacent to the chest. Acoustic waves 4H are converted into electrical signals as known per se thus not detailed here. It should be noted that acoustic waves 4H can be sensed without trouble through a light clothing, an underwear or the like.

According to one particular option, the device is further equipped with an ECG function, i.e. ElectroCardioGraphic function.

For this purpose there are provided three contact electrodes 31, 32, 33, the three of them integrated in the device, without the need to have linking wires like in most prior art devices.

The first electrode 31 is arranged on the internal wall 86 of the band and has a sensitive face oriented toward the skin of the arm. The third electrode 33 is also arranged on the internal wall 86 and has also a sensitive face oriented toward the skin of the arm.

Each of the electrodes is formed as a thin pad of a surface comprised between 2 cm$^2$ and 10 cm$^2$; a surface between 5 cm$^2$ and 7 cm$^2$ can be chosen; the shape of the thin pad is somewhat curved to follow the standard curvature of the skin of the arm.

When the inner layer 1 is present, as exemplified in FIG. 5, the first and third electrodes 31,33 are placed on the outer face of the inner layer oriented toward the axis.

The first and third electrodes 31,33 are arranged at a cuff assembly distal end (second end 36) opposed to the interface member for example one aside the other transversally (along W). Alternatively, first and third contact electrodes 31, 33 can be arranged differently, for example one aside the other along L. In the shown example, there is provided a back pad 19 to support the contact electrodes 31, 33. The Lycra inner layer 1 is sandwiched at this place between the back pad 19 and the contact electrodes 31, 33.

Whenever the cuff assembly is pressurized, first and third contact electrodes 31, 33 are firmly pressed against the skin of the arm, thereby ensuring a fairly good contact with a small electrical contact resistance. It should be noted that no gel is required at the contact electrode contrary to prior art habits, Contact electrodes are to be placed against the bare skin; however, thanks to the pressure, it is not excluded to have a light underwear cloth between the skin and the electrodes.

The contact electrodes can be made of stainless steel, silver, or other coated materials (coated with silver, chromium, gold, titanium or platinum), not excluding materials coated by physical vapor deposition technique (known as PVD techniques). The contact electrodes can also be made of a conducting wire (stainless steel, silver, etc.) sewed to the inner layer.

It is to be noted that two electrodes might be sufficient, therefore the third electrode 33 is considered optional.

Regarding the second electrode 32, it is arranged around the external surface of the control unit assembly as best seen at FIG. 4. A conductive material forms a coating of at least a part of the control unit housing. A metallic coating material (silver, titanium, chromium), are deposited by physical vapor deposition technique (known as PVD techniques). It can also be an empty cylinder made out of the conductive material.

In one example, the second electrode covers the lower third of the cylinder, for example all around the accessible circumference by the fingers of the user (see FIG. 1). Therefore, it is easy for the user to grab/seize the second electrode with a good electrical contact. According to one example, the second electrode lies over the 20% lower part of the control assembly unit; in other implementation, its height can be bigger, like 30% or 40%.

The device further comprises connection wires to provide electrically coupling between sensors and the control unit housing 7. Connection wires 44,45 electrically couple the contact electrodes with the control unit housing.

Connection wires 49 electrically couple the acoustic sensor with the control unit housing 7. The connection wires are integrated into the cuff assembly and they are protected therein and not visible from the outside. As depicted at FIG. 5, since the connection wires are arranged at an outer zone of the bladder, for example between the intermediate sheet (4), and the outer band (5), they do not hinder inflation and measurement.

Further, we note that the in between position of the connection wires provides protection against mechanical risks.

Interface Member

Figure 6:
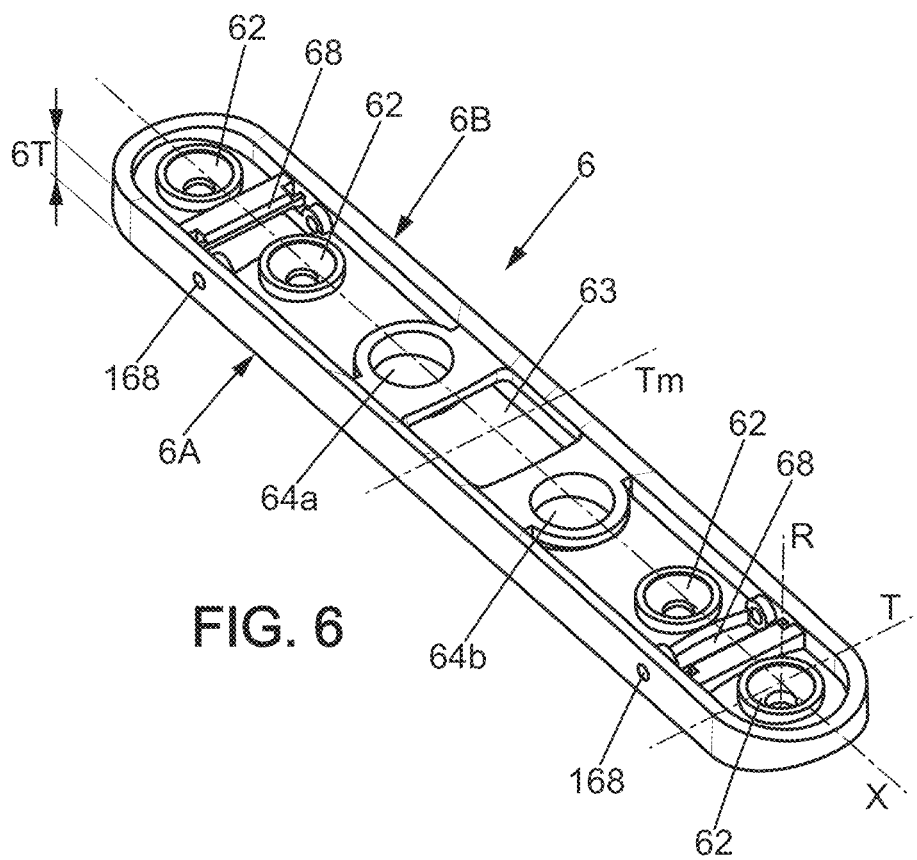
FIG. 6 is a perspective view of an example of the interface member.
Figure 7:
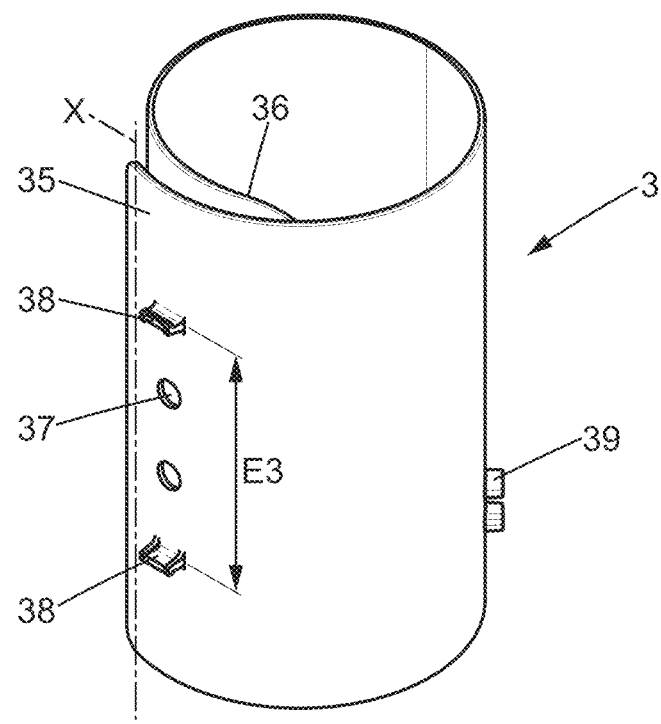
FIG. 7 is a perspective view of an example of resilient cuff holder.
Figure 8:
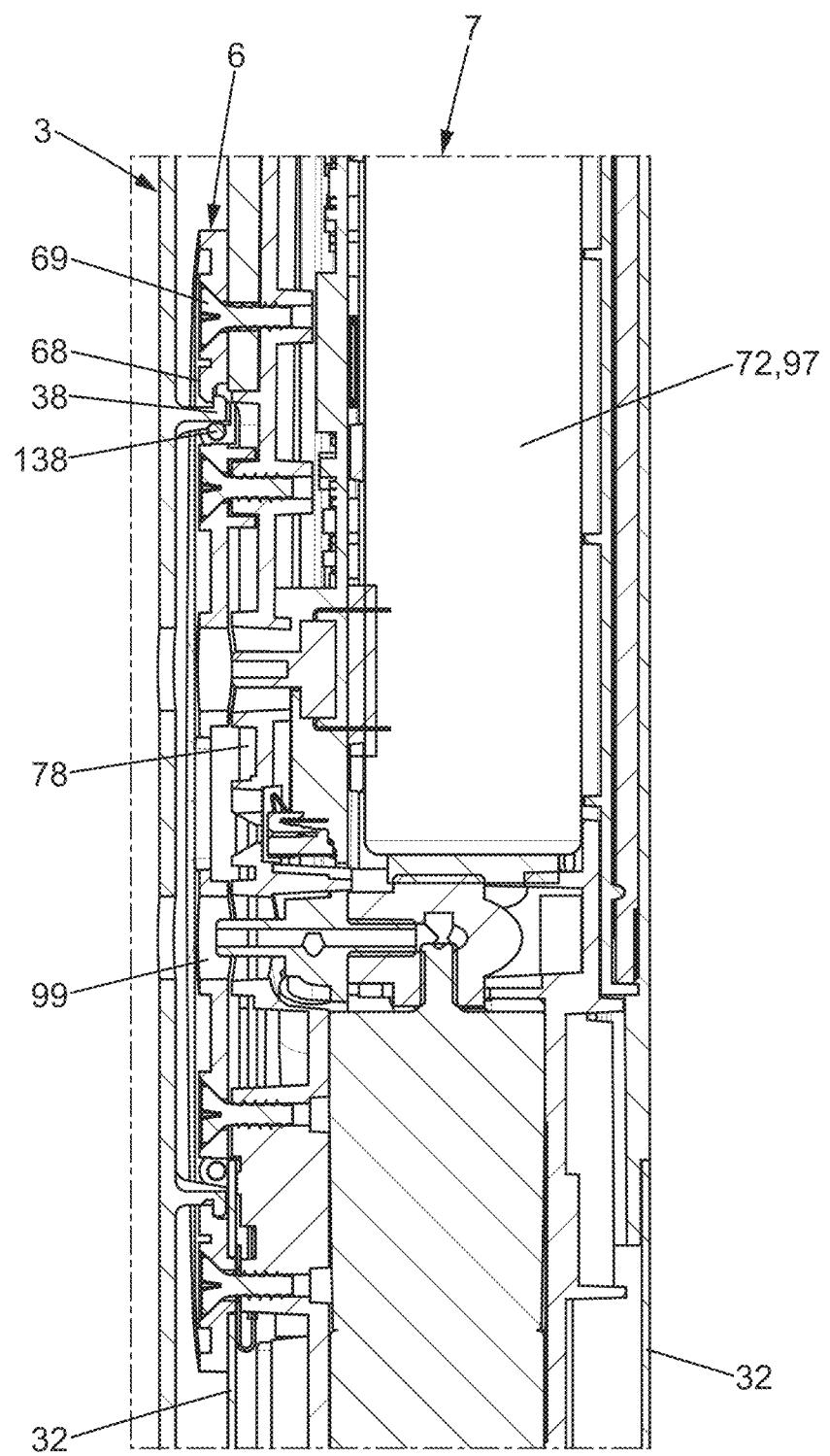
FIG. 8 is an enlarged view of the interface area, also illustrating the interlocking function.

As already mentioned, with reference to FIG. 6, the assembling direction is denoted R, the elongation axis of the interface member is denoted X, the transverse direction of the interface member is denoted T. Tm designates a median plan parallel to R and T.

According to the illustrated example, the interface member 6 is a part interposed between the control unit housing and the cuff assembly for securing them together.

Figure 9:
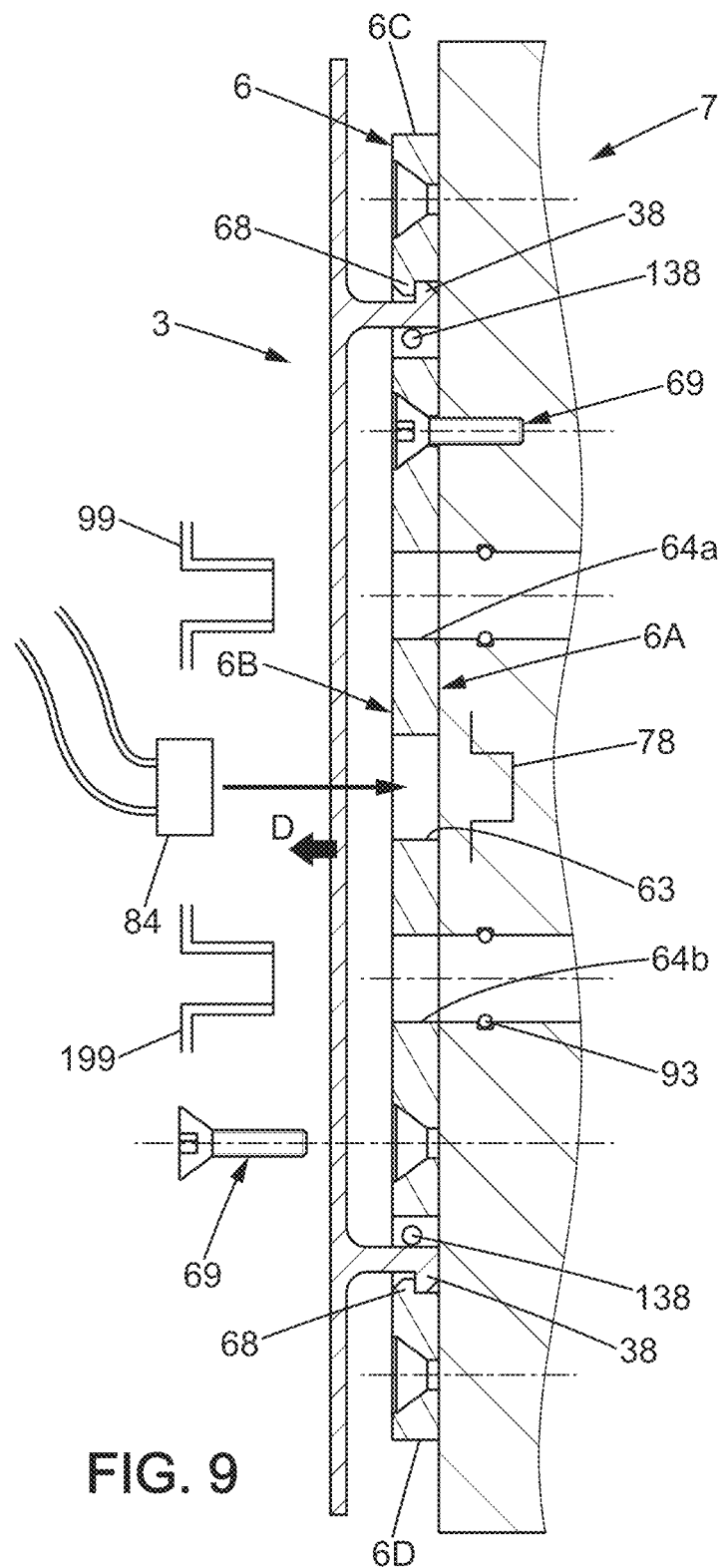
FIG. 9 shows a sectional view of the interface member and associated elements.
Figure 10:
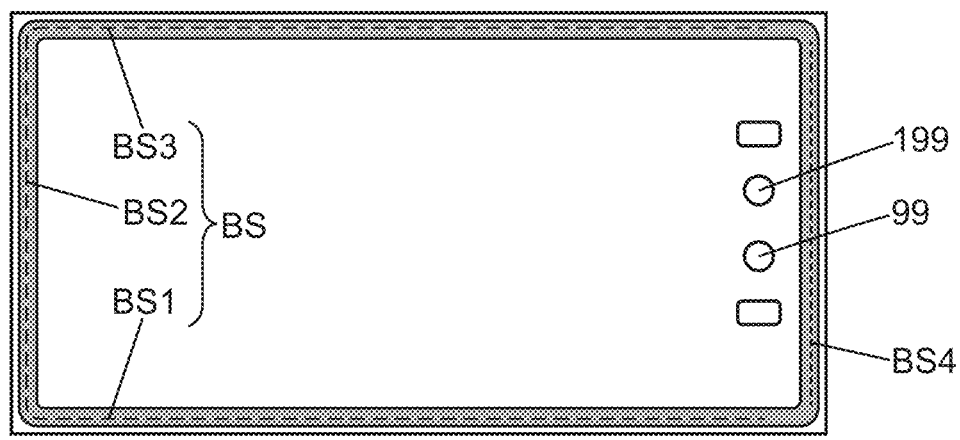
FIG. 10 shows a schematic top view of the bladder and the border seams.

As illustrated at FIGS. 6 and 9, the interface member 6 is screwed to the control unit housing. More precisely, there are provided through holes 62 in the interface member.

Screws 69 are provided to fix the interface member to the control unit housing.

In the shown example, the through holes 62 are frustoconical thru bore, and the proposed screws are of the type countersunk head screw.

There is provided in a middle portion of the interface member at least a through hole 63 for electrical wire connection/coupling, two through holes 64a,64b for pneumatic fluid piping/coupling.

There is provided threaded holes in the body of the control unit housing 7 for receiving the screws 69. There may be provided 2 or 4 screws in the attachment (4 illustrated).

The interface member 6 comprises two complementary retaining members 68, configured to be snap-fit with the retaining members 38. Here the complementary retaining members are in the form of shoulders or elbows, i.e. stop abutments preventing retaining members from moving away from the control unit housing.

The interface member 6 comprises transverse holes 168 arranged in the transverse direction T for receiving the interlock pins 138. The interlock pins prevent disassembly of complementary retaining members 68 versus retaining members 38. Said interlock pins 138 and transverse holes 168 have for example a diameter less than 2 mm, therefore, this is nearly hidden and difficult to tamper.

The interface member 6 exhibits a first face 6A oriented towards the control unit housing 7 and a second face 6B oriented towards the cuff assembly.

The first face 6A is concave and is configured to follow the cylindrical body of the control unit housing. The second face 6B is substantially flat or exhibits a slight concavity.

The longitudinal ends of the interface member denoted respectively 6C and 6D. The distance between the two ends 6C,6D is at least 10 cm or two-thirds of the height H1 of the cuff-holder.

There is provided a connector 84 attached to the connection wires. In one example, the connector is a flat flex PCB-type connector. The connector is inserted through the central through hole 63, and is plugged onto a corresponding counterpart electrical socket 78 provided in the control unit housing.

Regarding the pneumatic connections, there may be provided O-rings 93 in the control unit housing or likewise complementary tubes, such that the connection ports 99,199 are received in an airtight manner into pneumatic components of the control unit housing.

Attachment Band

There is provided an attachment band 8, The attachment band 8 extends from the cuff assembly along a longitudinal direction L configured to momentarily secure the attachment band to the outer band of the cuff assembly during a measurement cycle.

At FIG. 5, the attachment band 8 is represented intentionally shorter than real, thanks to chain-dot inter lines.

The attachment band 8 is flexible and comprises fixing means for securing that number to the external wall 87 of the cuff assembly 18 at least during the blood pressure measurement. The proper position is chosen by the user according the size of his/her arm.

In one configuration, the fixing means may comprise loop and hook pads, a loop pad 88 at one location and a hook pad 89 at another counterpart location, such that adjustment and securing of various encompassed circumferences (π D2) of user's arm is made available. This allows convenient attachment whatever the size of the arm.

Overall System

The control unit housing 7, the attachment band 8 and the cuff assembly 18 have substantially the same height (H1, H3,H7) along the transverse axis W. This provides an aesthetic assembly and eases rollup configuration. This configuration allows optimization of the occupied volume.

As shown at FIG. 2, the control unit housing 7 and the acoustic sensor 90 are arranged at an angle α comprised between 90° and 140° with regard to the cylindrical configuration of the cuff assembly, as defined in a use configuration on a 30 cm reference arm circumference. As shown at FIG. 11, there is provided a wireless coupling E8 with smartphone E5. It is to be noted that the switch 71 can be physical switch, or tap switch or a tactile area.

The invention claimed is:

1. A cuff-type monitoring device, for collecting cardiovascular data relating to an individual user, comprising a control unit housing and a cuff assembly coupled to the control unit housing, the cuff assembly comprising, from an inner item to an outermost item:
    an inflatable bladder,
    an cuff holder, forming an structural resilient armature of the cuff assembly,
    an intermediate sheet,
    an outer band,
    wherein the cuff assembly is configured, in use, to surround an upper limb of the individual,
    wherein the control unit housing comprises at least a pump configured to inflate the inflatable bladder,
    wherein the intermediate sheet is made in an inextensible, i.e. non-stretchable, fabric, and
    wherein the inflatable bladder and the intermediate sheet are two distinct items.

2. The device according to claim 1, wherein here is provided a first opening in the intermediate sheet and, in the outer band to let the passage for at least one fluid port of the inflatable bladder.

3. The device according to claim 1, wherein the intermediate sheet exhibits a Young modulus not less than 1 giga Pascals.

4. The device according to claim 1, wherein the cuff holder is a resilient plastic sheet, with a first longitudinal end coupled to the control unit housing and a second end having a tapered end portion.

5. The device according to claim 1, further comprising an attachment band, extending from the cuff assembly along a longitudinal direction, the attachment band being flexible and having an adjustable fastener configured to momentarily secure the attachment band to the outer band of the cuff assembly during a measurement cycle.

6. The device according to claim 1, wherein the control unit housing the attachment band and the cuff assembly have substantially the same height along the transverse axis.

7. The device according to claim 1, wherein the control unit housing comprises a pneumatic unit which comprises a discharge valve, a check valve, and a pressure sensor.

8. The device according to claim 7, wherein the control unit housing comprises an electronic controller configured to control the pneumatic unit and to determine at least the arterial pressure of the user, an On/Off switch and a display.

9. The device according to claim 1, further comprising:
    an acoustic sensor coupled to the external wall of the cuff assembly and having a sensitive side oriented away from the internal wall of the cuff assembly; and
    connection wires to electrically couple the acoustic sensor with the control unit housing, whereby the connection wires are arranged at an outer zone of the bladder between the intermediate sheet and the outer band.

10. The device according to claim 1, wherein the cuff holder is interposed between the inflatable bladder and the intermediate sheet.

11. The device according to claim 1, wherein the intermediate sheet is interposed between the cuff holder and the outer band.

12. The device according to claim 1, wherein the inflatable bladder, the intermediate sheet and the outer band are secured together.

13. The device according to claim 1, wherein there is provided a border joint at least on three sides on a peripheral border of the inflatable bladder, the border joint joining and securing together the inflatable bladder, the intermediate sheet, and the outer band.

14. The device according to claim 13, wherein the cuff assembly further comprises, as innermost item, an inner layer, configured to come in contact, directly or via a clothing, with the upper limb, and wherein the border joint joins and secures said inner layer together with the inflatable bladder, the intermediate sheet, and the outer band.

15. The device according to claim 13, wherein the border joint is a border seam.

16. The device according to claim 1, further comprising:
at least one contact electrode for electrocardiographic sensing, being arranged at a distal extremity on an internal wall of the cuff assembly to contact an arm skin of a device user.

17. The device according to claim 16, further comprising:
connection wires to electrically couple the at one least contact electrodes with the control unit housing, whereby the connection wires are arranged between the intermediate sheet and the outer band.

18. The device according to claim 17, whereby the connection wires are arranged at an outer zone of the inflatable bladder.

19. The device according to claim 1, further comprising
as innermost item, an inner layer, configured to come in contact, directly or via a clothing, with the upper limb,
at least one contact electrode for electrocardiographic sensing, being arranged on an outer face of the inner layer of the cuff assembly, to contact an arm skin of a device user,
a back pad, to support the at least one contact electrode, wherein the inner layer is sandwiched between the back pad and the contact electrode.

\* \* \* \* \*